United States Patent [19]
Ritscher et al.

[11] Patent Number: 5,250,490
[45] Date of Patent: Oct. 5, 1993

[54] NOBLE METAL SUPPORTED ON A BASE METAL CATALYST

[75] Inventors: James S. Ritscher, Marietta, Ohio; Wei T. Yang, Belle Mead, N.J.; George M. Omietanski, Marietta, Ohio; Robert L. Ocheltree, Pennsboro; Earl E. Malson, New Martinsville, both of W. Va.

[73] Assignee: Union Carbide Chemicals & Plastics Technology Corporation, Danbury, Conn.

[21] Appl. No.: 813,083

[22] Filed: Dec. 24, 1991

[51] Int. Cl.$^5$ .................. B01J 23/60; B01J 23/64; B01J 23/89
[52] U.S. Cl. .................. 502/313; 502/324; 502/325; 502/326; 502/331; 502/339
[58] Field of Search .............. 502/313, 324, 325, 326, 502/329, 331, 339

[56] References Cited

U.S. PATENT DOCUMENTS

| | | | |
|---|---|---|---|
| 3,793,224 | 12/1970 | Cooper | 252/423 |
| 3,806,466 | 7/1971 | Bird | 252/422 |
| 3,882,050 | 5/1972 | Niebylski | 502/326 |
| 3,979,329 | 2/1974 | Cooper | 252/422 |
| 3,992,512 | 12/1974 | Petrow | 423/512 |
| 4,299,192 | 5/1979 | Enga | 122/4 D |
| 4,609,608 | 2/1985 | Sole | 430/106.6 |
| 4,623,635 | 11/1985 | Paparizos et al. | 502/339 X |
| 4,634,468 | 5/1985 | Gulla | 106/1.11 |
| 4,681,963 | 12/1986 | Lewis | 556/453 |
| 4,705,765 | 3/1987 | Lewis | 502/152 |
| 4,725,314 | 9/1987 | Gulla | 106/1.11 |
| 4,743,577 | 5/1988 | Schroeder et al. | 502/339 X |
| 4,921,988 | 12/1988 | Takatsuna et al. | 556/413 |

FOREIGN PATENT DOCUMENTS

| | | | |
|---|---|---|---|
| 49-119887 | 11/1974 | Japan | 502/326 |
| 0321174 | 12/1988 | Japan . | |
| 1-319683 | 12/1989 | Japan . | |
| 0053884 | 11/1981 | United Kingdom . | |

OTHER PUBLICATIONS

Bond, G. C., *Catlysis by Metals*, Academic Press, (New York: 1962), pp. 29–47.

Bond, G. C., *Small Particles of the Platinum Metals, Their Preparation, Characterisation, and Use in Catalysis*, Platinum Metal Review, vol. 19 (1975), pp. 126–134.

Bond, G. C., *The Reaction of Ethylene with Deuterium Over Various Types of Platinum Catalyst*, Faraday Society Transactions, vol. 52, (1956), p. 1235.

Boutonnet, Magall, et al., *Monodispersed Colloidal Metal Particles from Non-Aqueous Solutions: Catalytic Behaviour for the Hydrogenation of But-1-ene of Platinum Particles in Solution*, Applied Catalysis, vol. 20 (1986), pp.163–177.

Boutonnet, Magali, et al., *The Preparation of Monodisperse Colloidal Metal Particles From Mico-emulsions*, Colloids and Surfaces, vol. 5 (1982), pp. 209–225.

Bradley, John S., et al., *Clusters, Colloids and Catalysis*, J. Molecular Catalysis, vol. 41 (1987), pp. 59–74.

Brugger, Pierre-Alain, et al., *Ultrafine and Specific Catalysts Affording Efficient Hydrogen Evolution from Water under Visible Light Illumination*, J. Am. Chem. Soc., vol. 103 (1981), pp. 2923–2927.

Furlong, D. Neil, et al., *Colloidal Plantium Sols: Preparation, Characterization and Stability Towards Salts*, J. Chem. Soc., Faraday Transactions, vol. 8, (1984), pp. 571–588.

(List continued on next page.)

*Primary Examiner*—W. J. Shine
*Attorney, Agent, or Firm*—B. L. Deppenbrock

[57] ABSTRACT

The present invention provides an electroless process for making a catalyst in a liquid or gaseous medium comprising contacting a base metal with a chemical cleaning agent and simultaneously or sequentially treating said base metal under reducing conditions with a noble metal-containing material, the catalyst prepared using the process, and a method of using the catalyst.

24 Claims, No Drawings

OTHER PUBLICATIONS

Hirai, Hidefumi, *Formation and Catalytic Functionality of Synthetic Polymer-Noble Metal Colloid*, J. Macromol. Sci.-Chem., vol. A13(5) (1979), pp. 633-649.

Hirai, Hidefumi, *Polymer Effect on Fine Metal Particles and Reactive Metal Complexes*, Makromol. Chem. Suppl., vol. 14 (1985), pp. 55-69.

Hirai, Hidefumi, et al., *Selective Hydrogenation of Cyclooctadienes Using Colloidal Palladium in Poly(-N-vinyl-2-pyrrolidone)*, Bull. Chem. Soc. Japan, vol. 58 (1985), pp. 682-687.

Kiwi, John, et al., *Hydrogen Evolution from Water Induced by Visible Light Mediated by Redox Catalysis*, Nature, vol. 281, No. 25 (Oct. 1979), p. 657.

Kiwi, John et al., *Protection, Size Factors, and Reaction Dynamics of Colloidal Redox Catalysts Mediating Light Induced Hydrogen Evolution from Water*, J. Am. Chem. Soc., 101:24, Nov. 21, 1979, pp. 7214-7216.

Lewis, Larry N., et al., *Platinum-Catalyzed Hydrosilylation-Colloid Formation as the Essential Step*, J. Am. Chem. Soc., vol. 108 (1986), 7227-7231.

Matijevic, E., et al., *Formation of Uniform Colloidal Iron (III) Oxides in Ethylene Glycol-Water Solutions*, Colloid & Polymer Sci., vol. 265 (1987), pp. 155-163.

Prignano, Andrea L., et al., *Silica-Supported Bis(trialkylphosphine) Plantinum Oxalates: Photogenerated Catalysts for Hydrosilation of Olefins*, J. Am. Chem. Soc., vol. 109 (1987), pp. 3586-3595.

NOBLE METAL SUPPORTED ON A BASE METAL CATALYST

BACKGROUND OF THE INVENTION

1. Field of Invention

The present invention relates to a supported noble metal catalyst useful in organic and organosilicon processes. More particularly, the present invention relates to a catalyst comprising at least one noble metal deposited on a low surface area base metal having utility in processes comprising carbon-hydrogen or carbon-silicon bond formation, especially hydrosilation processes comprising an Si—H reactant.

2. Prior Art

Catalysts are generally classified according to the phase relationship between the catalyst and the initial reactants. A heterogeneous catalyst is in a different phase (gaseous, liquid, or solid) as compared to the phase of the initial reactants. A homogeneous catalyst is in the same phase as the reactants.

Noble metal catalysts can be either heterogeneous or homogeneous. Further, heterogeneous noble metal catalysts can be unsupported or supported on a carrier comprised of an inert solid material such as a metal oxide, as illustrated by alumina, or a base metal.

In general heterogeneous noble metal catalysts, supported and unsupported, have the advantage of being easily removed from a reaction, such as, for example, by filtration. Such facile removal of the heterogeneous noble metal catalyst can further result in the catalyst being re-used in the same reaction or recovered and used in a different reaction. Such advantages increase the overall efficiency of the catalyst and/or provide cost savings. Heterogeneous noble metal catalysts can be physically attached or fixed in different locations in the equipment in which the reaction is conducted. Heterogeneous noble metal catalysts, including metal oxide supported catalysts, are also readily susceptible to chemical promotion or activity modifications. However, such catalysts generally have the disadvantages of having large agglomerates of metal, and, hence, a much lower level of catalytic activity is observed as compared to homogeneous noble metal catalysts.

Although homogeneous noble metal catalysts usually have the advantage of being more active than heterogeneous noble metal catalysts, a homogeneous noble metal catalyst is usually in the form of a solution and is by definition interspersed among the initial reactants, making separation disadvantageously difficult.

Homogeneous noble metal catalysts must actually be considered as two distinct groups: those that are truly homogeneous, consisting of single atoms or ions of noble metals, and those consisting of agglomerates, frequently called clusters or colloids, of noble metals. The colloids are in solution and cannot be easily separated, as by filtration, and are commonly referred to as colloidal homogeneous noble metal catalysts. In most organosilicon processes, and many organic processes, the homogeneous noble metal catalyst is colloidal.

Means of differentiating these three types of noble metal catalysts, heterogeneous, homogeneous, and colloidal homogeneous, are discussed by L. N. Lewis and N. Lewis in Journal of the American Chemical Society, Volume 108, page 7228 (1986). Both a heterogeneous noble metal catalyst and a truly homogeneous noble metal catalyst are unaffected by mercury, while a colloidal noble metal catalyst is poisoned, i.e. no catalytic activity remains.

Surprisingly, the process of the present invention produces a catalyst having activity comparable to a colloidal homogeneous noble metal catalyst but, like a heterogeneous noble metal catalyst, it can be readily removed, reused, or recovered from the reaction zone and is susceptible to activity modifications. The catalyst of the present invention is used in organic processes such as hydrosilation, dehydrocondensation, deamination, amination, hydrogenation, dehydrogenation, and the like. That is, the catalyst of the present invention can be substituted for a colloidal homogeneous noble metal catalyst that may be presently used in these processes. In many of these processes, the colloidal homogeneous noble metal catalyst is non-recoverable. The catalyst prepared in accordance with the process of the present invention is recoverable and reusable which can be a significant processing advantage in these processes.

SUMMARY OF THE INVENTION

The present invention provides an electroless process for making a catalyst in a liquid or gaseous medium comprising (1) contacting a base metal with a chemical cleaning agent, and (2) treating said base metal under reducing conditions with a noble metal-containing material.

The contacting and treating steps can be carried out simultaneously or sequentially.

The present invention also provides a catalyst prepared according to the aforementioned process and a method of using the catalyst.

DETAILED DESCRIPTION OF THE INVENTION

The process of the present invention is electroless (non-electrolytic) and produces a catalyst having a noble metal deposited, or fixed in place, on a base metal. The catalyst so produced behaves or has the advantages of a heterogeneous noble metal catalyst but also exhibits catalytic activity similar to a colloidal homogeneous noble metal catalyst. The catalyst of the present invention can be employed in any process in which the process or reaction takes place in the presence of a colloidal homogeneous noble metal catalyst. Such processes include, for example, hydrosilation, dehydrocondensation, deamination, amination, hydrogenation, dehydrogenation, hydroformylation, and the like, especially hydrosilation reactions comprising an Si—H reactant. In these processes the catalyst of the present invention is employed in place of a colloidal homogeneous noble metal catalyst and contains substantially the same amount of noble metal or an excess of noble metal.

Base Metal

The base metal can be in any desired physical shape. For example, the base metal can be a powder, chips, a shaped metal piece such as a wire, a strip, a coil, sheet, or wire gauze. In general, the form or shape of the base metal depends on the design of the reactor employed and/or on the type of reaction to be effected. Determining the shape or form of the base metal based upon the type of reactor and the reaction in which it will be employed is known to one of ordinary skill in the art. For example, a powder would generally be used to catalyze a gas phase organic reaction in a fluidized bed. Shaped metal pieces, such as sheets, wire gauze, or spiral windings would generally be employed for a liquid phase organic reaction in a tubular reactor. Three phase reactors, such as a bubbling column reactor can effectively use powder or wire gauze forms of base metal for catalyzing reactions.

Base metals that are suitably employed in the present invention are selected from the group consisting of titanium, vanadium, chromium, manganese, molybdenum, tungsten, iron, cobalt, nickel, copper, zinc, alloys and mixtures thereof. Preferably, the base metal is selected from the group consisting of iron, nickel, chromium, alloys and mixtures thereof. By "alloy" is meant a mixture of a base metal with another base metal, a mixture of a base metal with a metal other than a base metal, or a mixture of a base metal with a nonmetal, such as, for example, carbon. Most preferably the base metal is iron, nickel, and their respective alloys, such as, for example, steel. In general, the base metals employed herein have a low surface area, i.e., less than 1 square meter per gram.

Chemical Cleaning Agent

The surface of the base metal is treated with a chemical cleaning agent prior to or at the same time the surface is contacted with a noble metal. Pretreating or simultaneously treating the base metal with a chemical cleaning agent, or etchant, increases catalytic activity. Suitable chemical cleaning agents can be selected from the group consisting of a chlorosilane, an alkoxysilane, an acid, and mixtures thereof. Preferably, the chlorosilane, when employed, is selected from the group consisting of trichlorosilane, tetrachlorosilane, and methyldichlorosilane. Preferably, an alkoxysilane, when employed, is selected from the group consisting of trimethoxysilane, triethoxysilane and methyldimethoxysilane. In general, acids having a dissociation constant greater than $1 \times 10^{-4}$, which are non-oxidizing and do not form insoluble salts of the base metal, are suitably employed in the present invention. When an acid is employed, preferably it is selected from the group consisting of hydrochloric acid and acetic acid. Since a solution of the noble metal-containing material is often acidic, the solution can serve as the chemical cleaning agent. For example, chloroplatinic acid can provide not only the noble metal for deposition but can also serve as the chemical cleaning agent. However, when such a noble metal-containing solution is employed, generally a higher concentration is desirable than when a non-noble metal-containing chemical cleaning agent is used.

If an acid is selected as the cleaning agent, it is used in an amount of 1 to 10 times the weight of noble metal to be deposited. If a chlorosilane or alkoxysilane is chosen, it is used in an amount at least equal to and preferably at least 10 times, the weight of noble metal to be deposited.

Noble Metal-Containing Material

In the electroless process of the present invention, the surface of the base metal is contacted with a noble metal-containing material. Usually, the base metal is contacted with a liquid solution of the noble metal. However, the base metal can be suitably contacted with a gaseous or volatile noble metal-containing material.

When the base metal is contacted with a homogeneous noble metal solution, the noble metal is selected from the group consisting of a noble metal halide, a noble metal-containing complex, or a salt of a noble metal halide contained in a solvent. By homogeneous is meant that the noble metal halide, salt or complex is dissolved in a solvent which is preferably a liquid. Noble metals that can be employed in the present invention are selected from the group consisting of platinum, iridium, ruthenium, rhodium, palladium and mixtures thereof. Preferably, the noble metal is selected from the group consisting of platinum, rhodium, palladium and mixtures thereof.

Illustrative noble metal halides, complexes and salts are as follows:

Platinum halides and salts thereof, such as, for example, $H_2PtCl_6$, $PtCl_4$, $Na_2PtCl_6$, $Na_2PtCl_4$ and mixtures thereof in solvents such as water, cyclic and linear ethers, alcohols and mixtures thereof. Preferred solvents include tetrahydrofuran, 2-propanol, ethanol, and 1,2-dimethoxyethane and mixtures thereof. Most preferred is chloroplatinic acid in an ethanol/1,2-dimethoxyethane mixture.

Platinum complexes such as, for example, Pt(2,4-pentanedioate)$_2$ and PtCl$_2$(triphenylphosphine)$_2$ and mixtures thereof in solvents such as, for example, aromatic hydrocarbons and chlorinated aliphatic and aromatic hydrocarbons and mixtures thereof. Preferred solvents include methylene chloride, toluene, and o-dichlorobenzene and mixtures thereof. Most preferred is Pt(2,4-pentanedioate)$_2$ in one or more of the preferred solvents (methylene chloride, toluene, o-dichlorobenzene).

Palladium halides and salts thereof such as, for example, $PdCl_2$, $Na_2PdCl_4$, $Na_2PdCl_6$ in solvents such as water and aliphatic alcohols having one to three carbon atoms and mixtures thereof. Preferred solvents include water and methanol and mixtures thereof. A preferred palladium halide is $PdCl_2$ in water, methanol or a mixture thereof.

Palladium complexes such as, for example, Pd(acetate)$_2$, PdCl$_2$(triphenylphosphine)$_2$ and Pd(trifluoroacetate)$_2$ in solvents such as, for example, chlorinated hydrocarbons having 1 to 6 carbon atoms and linear and cyclic ethers having 4 to 6 carbon atoms and mixtures thereof.

Ruthenium halides and salts thereof such as, for example, $RuCl_3$, $(NH_3)_2RuCl_6$, $K_2RuCl_5$, and $Ru(NO)Cl_3$ in solvents, such as, for example, water, linear or branched aliphatic alcohols having 1 to 3 carbon atoms, linear and cyclic ethers having 4 to 6 carbon atoms and mixtures thereof. Preferably the ruthenium halide is $RuCl_3$ and the preferred solvent is ethanol or tetrahydrofuran.

Ruthenium complexes such as, for example, Ru$_3$(CO)$_{12}$ and RuCl$_2$(1,5-cyclooctadiene), of which Ru$_3$(CO)$_{12}$ is preferred. Note: Ru$_3$(CO)$_{12}$ is volatile and does not require a solvent. RuCl$_2$(1,5-cyclooctadiene) can be dissolved in aromatic hydrocarbons and chlorinated aliphatic and aromatic hydrocarbons.

Rhodium halides and salts thereof such as, for example, $RhCl_3$, $Na_3RhCl_6$, $(NH_3)_3RhCl_6$ in solvents such as, for example, water, linear or branched aliphatic alcohols having 1 to 3 carbon atoms, and linear and cyclic ethers having 4 to 6 carbon atoms. The preferred rhodium halide is $RhCl_3$; and the preferred solvents are water, ethanol, and 1,2-dimethoxyethane, and mixtures thereof.

Rhodium complexes such as, for example, [RhCl(CO)$_2$]$_2$, [RhCl(norbornadiene)]$_2$, Rh$_2$(acetate)$_4$, and Rh$_4$(CO)$_{12}$. Note: the rhodium carbonyl complex is volatile and does not need a solvent. Suitable solvents for other rhodium complexes include, for example, aromatic hydrocarbons and chlorinated aliphatic and aromatic hydrocarbons and mixtures thereof.

Iridium halides and salts thereof such as, for example, $H_2IrCl_6$, $Na_3IrCl_6$, and $K_2IrCl_6$. A preferred iridium halide is $H_2IrCl_6$. Suitable solvents include for example, water, linear and branched aliphatic alcohols having 1 to 3 carbon atoms, and linear and cyclic ethers and mixtures thereof. Preferred solvents include water, ethanol, and 1,2-dimethoxyethane and mixtures thereof.

Iridium complexes such as, for example, $IrCl(CO)_3$, $[IrCl(1,5-cyclooctadiene)]_2$, and $Ir_4(CO)_{12}$. A preferred iridium complex is $[IrCl(1,5-cyclooctadiene)]_2$. Note: the iridium carbonyl complex is volatile and does not need a solvent. Suitable solvents for other iridium complexes include, for example, aromatic hydrocarbons and chlorinated aliphatic and aromatic hydrocarbons and mixtures thereof.

In general, the amount of noble metal halide, salt, or complex used is 0.02-2.0 percent by weight of the charge of base metal. A charge of 0.02-0.2 percent is preferred.

Reducing Conditions

In the present invention, by "reducing conditions" is meant the presence of a chemical specie capable of irreversibly donating electrons to a noble metal specie having a higher valence or oxidation state. The base metal itself can serve as the chemical reducing agent. When the reduction potential of the base metal has a higher value than the reduction potential of the noble metal according to the electronegativity scale, the base metal can serve as the reductant, and another chemical reducing agent is not needed. For example, titanium, having one of the highest ratings on the electronegativity scale, if rendered clean by a chemical agent, can serve as a reducing agent. Additionally, in accordance with another embodiment of the process of the present invention, the surface of the base metal is contacted with the homogeneous solution of the noble metal halide, salt, or complex in the presence of a chemical reducing agent.

When a chemical reducing agent other than the base metal is employed, it can be formaldehyde or a silane having the general formula $(R)_ySi(H)_x$, wherein x and y are each individually at least 1, $x+y=4$, and R is the same or different and is selected from the group consisting of a halogen, an alkoxy having 1 to 5 carbon atoms, an alkyl having 1 to 6 carbon atoms, and a haloalkyl having 1 to 4 carbon atoms. Accordingly, when the chemical reducing agent is a silane, it is selected from the group consisting of a hydridoalkoxysilane, a hydridohalosilane, a hydridoalkylalkoxysilane, and a hydridoalkylhalosilane. Preferably, the chemical reducing agent is selected from the group consisting of trichlorosilane, methyldichlorosilane, trimethoxysilane, triethoxysilane, methyldimethoxysilane and mixtures thereof. Also useful as the reducing agent are hydridosiloxanes and other silanic-hydrogen fluids such as, for example, 1,1,1,2,3,3,3-heptamethyltrisiloxane or a poly(dimethyl)(methylhydrogen)siloxane.

The amount of reducing agent used must be in excess of the molar equivalent of noble metal salt or complex, and a minimum ten-fold excess is preferred.

Use of the Catalyst of the Present Invention in Hydrosilation

The catalysts prepared in accordance with the process of the present invention are useful in effecting hydrosilations, which hydrosilation processes are well known in the art. In general, hydrosilations in which a catalyst of the present invention is employed are conducted by adding a hydridosilane or hydridosiloxane to an olefinic substrate (reactant) in the presence of a platinum or other noble metal catalyst prepared in accordance with the process of the present invention at ambient temperature up to 125° C., preferably 60° to 90° C., most preferably 75° to 85° C., and at autogenous pressure Higher pressure can be employed if the olefinic substrate is a low boiling compound. Alternatively, the olefinic substrate can be added to the hydridosilane or hydridosiloxane in the presence of a noble metal catalyst of the present invention such as a platinum-containing catalyst. In instances where it is desired to produce a copolymer, it is sometimes found convenient by those skilled in the art to mix or combine a silanic-hydrogen fluid and the olefinic substrate, heat the mixture to 60° to 125° C., preferably 60° to 90° C., and most preferably 75° to 85° C., and then add the noble metal catalyst which is preferably a platinum-containing catalyst.

U.S. Pat. No. 4,614,812 discloses the addition of a catalyst to a mixture of an olefin and a hydrosilane or hydrosiloxane; as well as, the addition of an olefin to a hydrosilane or hydrosiloxane in the presence of a catalyst. U.S. Pat. No. 5,041,595 discloses the addition of a hydrosilane to an excess of olefin in the presence of a catalyst.

The particular noble metal catalyst of the present invention employed in hydrosilation depends on the structure of the olefinic substrate and whether or not the Si—H containing reactant contains multiple Si—H bonds. In general, a platinum-containing catalyst of the present invention is used in reactions utilizing alpha-olefins and monohydridosilanes and/or monohydridosiloxanes. Generally, a rhodium-containing catalyst of the present invention is used in reactions utilizing polyhydridosilanes and/or polysubstituted olefins. When a ruthenium-containing catalyst of the present invention is used in hydrosilation processes traces of oxygen can be used.

A. Onopchenko and E. T. Sabourin disclose the role of oxygen in promoting catalysis of hydrosilation processes that employ platinum in the *Journal of Organic Chemistry*, Volume 52, pages 4118-4121 (1987). The role of oxygen in promoting catalysis of hydrosilation processes that employ rhodium is disclosed by H. M. Dickers in the *Journal of the American Chemical Society*, Volume 108, pages 7228-7231 (1986). Hydrosilation processes employing collodial noble metal catalysts are disclosed in U.S. Pat. Nos. 4,705,765 and 4,921,988; European Pat. No. 0-321,174-A2; and in the *Journal of the American Chemical Society*, Volume 108, pages 7228-7231 (1986).

The catalyst of the present invention is employable in hydrosilation processes known to employ a colloidal homogeneous noble metal catalyst selected from the group consisting of platinum, rhodium, ruthenium, palladium, and iridium. Preferably the catalyst is platinum, rhodium or ruthenium. Most preferably, the catalyst is a platinum-containing catalyst such as prepared using chloroplatinic acid. It is especially preferred to use the catalyst of the present invention in hydrosilation processes which use at least one substrate selected from the group consisting of acetylene, allyl glycidyl ether, allylamine, allyl chloride, 1-alkenes having 2 to 18 carbon atoms and allylpolyethers (preferably allylpolyethers having a molecular weight ranging from 200 to 4000).

Use of the Catalyst of the Present Invention in Reductive Amination and Reductive Deamination The catalysts prepared in accordance with the process of the present invention are useful in effecting reductive amination and reductive deamination, which processes are well-known reactions. In general, reductive amination in which a catalyst of the present invention is employed is the process whereby an organic substrate containing a carbonyl or cyano functionality is reacted with an approximately stoichiometric amount of an organic primary or secondary amine and excess hydrogen in the presence of a catalyst to yield a more highly substituted amine and byproduct, water or ammonia, respectively. For example, reductive amination takes place when a mixture such as a mixture of an aldehyde or ketone and ammonia or substituted amine is treated with hydrogen in the presence of a catalyst of the present invention. In reductive amination, the C≡N bond of the unstable imine intermediate is reduced and an amine results in accordance with the following reactions:

$$R_2CO + HNR'_2 + H_2 \rightarrow R_2CH-NR'_2 + H_2O \quad (I)$$

$$RCN + HNR'_2 + 2H_2 \rightarrow RCH_2-NR'_2 + NH_3 \quad (II)$$

wherein R and R' are individually the same or different and each can be an alkyl group having 1 to 18 carbon atoms or an aryl group. If a silane-containing substrate is used as is taught in U.S. Pat. No. 4,526,996, then byproduct water cannot be tolerated, and only a reactant containing cyano functionality is suitable.

Typically, in reductive amination which employs nitriles, excess ammonia is employed in the reaction to minimize any undesirable side reaction which can result in secondary amine formation. However, the side reaction may be exploited and used as a method for making secondary amines. This process is sometimes referred to as reductive deamination.

Although carbonyl-containing reactants are the most active, and, hence, the most preferred reactants, the incompatibility of water by-product with silanes makes the cyano-containing substrates the only suitable reactants when silane functionality is present. Silane-free substrates can be alkyl-, aralkyl-, aryl-aldehydes or alkyl-, aralkyl-, or aryl-ketones, and cycloaliphatic ketones. Illustrative of such compounds are benzaldehyde, isobutyraldehyde, dibenzylketone, and cyclohexanone. Preferred silane-containing substrates are cyanoethyltrialkoxysilanes, cyanoethylmethyldialkoxysilanes, and 4-trialkoxysilyl-2-methylbutanenitrile. Cyanoethyltrimethoxysilane and cyanoethyltriethoxysilane are most preferred.

In reductive amination reactions as practiced using the catalyst of the present invention, the preferred noble metal-containing catalysts are those heterogeneous catalysts, containing rhodium, palladium and platinum.

As practiced using the catalyst of the present invention, reductive deamination, also referred to as deaminative coupling, is the process of heating an organic amine substrate in the presence of hydrogen, a catalyst, and optionally a secondary amine, to yield a higher substituted amine product and ammonia byproduct. If the organic amine is primary, and no secondary amine is present, the product may be either the secondary or the tertiary amine, depending primarily on the catalyst chosen. The reaction takes place in accordance with the following equations:

$$2R_2CHNH_2 \rightarrow (R_2CH)_2NH + NH_3 \quad (III)$$

$$3R_2CHNH_2 = (R_2CH)_3N + 2NH_3 \quad (IV)$$

wherein R is the same as defined in Equation I. If a secondary amine is present, a tertiary amine can be formed by reaction with the primary amine substrate in accordance with the following equation:

$$R'_2NH + R_2CHNH_2 \rightarrow R_2CHNR'_2 + NH_3 \quad (V)$$

wherein R and R' are the same as defined in Equation I. Unless a large stoichiometric excess of secondary amine is used, the formation of the desired tertiary amine is not efficient, because the primary amine preferentially couples with itself in accordance with the reaction of Equation III.

Preferred substrates for use in conjunction with the catalyst of the present invention are 3-aminopropyltrialkoxysilanes, especially the trimethoxy and triethoxy esters.

Generally, in reductive deamination reactions using the catalyst of the present invention, palladium-containing noble metal catalyst is preferred for preparing secondary amines, and a platinum-containing catalyst is the preferred noble metal catalyst for preparing tertiary amines.

In general, reductive amination and reductive deamination using the catalyst of the present invention take place at temperatures ranging from about 100° to 250° C., preferably 150° to 200° C., and most preferably 170° to 190° C. Reductive amination reactions employing the catalyst of the present invention are conducted at a pressure ranging from about 100 to 700 psi, preferably 100 to 400 psi, and most preferably 200 to 400 psi. Reductive deamination reactions employing the catalyst of the present invention are conducted at a pressure ranging from autogenous to 100 psi, preferably autogenous to 25 psi, and most preferably at autogenous pressure.

The catalyst of the present invention can be used in any reductive amination or reductive deamination reaction or process in lieu of the colloidal homogeneous catalyst typically employed in such processes. When the catalyst of the present invention is substituted in these processes, the noble metal content of the catalyst of the present invention is present in the same amount or in excess of the amount contained in the prior art colloidal, homogeneous catalyst.

Use of the Catalyst of the Present Invention in Hydrogenation

The catalyst prepared in accordance with the process of the present invention is useful in hydrogenation, which process is well known in the art. Hydrogenation as practiced using the catalyst of the present invention is used for the conversion of an olefinic substrate having a carbon-carbon triple bond into a carbon-carbon double bond or the conversion of an olefinic substance having a carbon-carbon double bond into a carbon-carbon single bond. The olefinic substrate can be substituted or unsubstituted, linear, alicyclic, aromatic or alkylaromatic organic compound. For example, an alkyne can be converted into an alkene, an alkene into an alkane, an unsaturated alcohol into a saturated alcohol, and an unsaturated ester into a saturated ester. Hydrogenation processes, in general, are disclosed for example by P. N. Rylander in *Catalytic Hydrogenation Over Platinum Metals*, Academic Press, New York (1957).

In general, hydrogenation as conventionally practiced is of two types based upon the type of catalyst employed: heterogeneous (two phase) and homogeneous (one-phase). In both types the catalyst facilitates the addition of molecular hydrogen ($H_2$), usually present in excess, to the unsaturated bond.

In hydrogenation using the catalyst of the present invention, a solution of the olefinic substrate is agitated under pressure of hydrogen gas in the presence of a small amount of catalyst. Reaction takes place rapidly, and when completed, a solution containing the saturated product is filtered from the insoluble catalyst. The catalyst of the present invention employed in hydrogenation is a noble metal on a base metal catalyst containing platinum, palladium, rhodium or ruthenium. Catalysts of the present invention are useful in specific hydrogenation reactions such as reduction of nitro groups, aldehydes, and aromatic rings, as well as olefinic double bonds.

In general, conventional homogeneous hydrogenation employs catalysts which are organic complexes of metals such as rhodium or iridium and which are soluble in organic solvents. Thus, in general, conventional homogeneous hydrogenation takes place in a single phase, the solution. By using the catalyst of the present invention in such a process, thus having two phases, it is easy to separate the catalyst from the product once the reaction is completed. Conventional homogeneous hydrogenation processes additionally may employ a catalyst promoter such as a carboxylic acid selected from the group consisting of acetic acid, formic acid, octanoic acid, stearic acid, propionic acid or other high boiling carboxylic acids which are known in the art. These promoters are also effective with the catalyst of the present invention.

In general, hydrogenation reactions using the catalyst of the present invention are conducted at a pressure ranging from autogenous pressure to 6000 psi, preferably autogenous pressure to 2000 psi, and most preferably 60 psi to 1000 psi.

Temperatures for hydrogenation using the catalyst of the present invention range from ambient temperature to as high as 200° C., with the preferred range being ambient temperature to 100° C., most preferred ambient temperature to 60° C.

Use of the Catalyst of the Present Invention in Dehydrogenation

The catalyst prepared in accordance with the process of the present invention is useful in dehydrogenation. Dehydrogenation is a well known process in which molecular hydrogen ($H_2$) is eliminated from linear and cycloaliphatic compounds to yield an aromatic compound. Conventionally a linear or cycloaliphatic compound is heated in the presence of a noble metal catalyst under low partial pressure of hydrogen which serves to activate the catalyst. Commonly preferred starting compounds are five-to-seven-member ring cycloalkenes, their mixtures and alkyl-substituted derivatives thereof. Cyclohexenes are most often preferred. The hydrogen so produced is vented, or removed by reaction with excess olefin, from the reaction. In general, the catalyst conventionally employed is unsupported platinum or palladium, or platinum or palladium supported on carbon or alumina.

Catalysts of the present invention can be substituted for the homogeneous colloidal platinum or palladium catalyst used in conventional dehydrogenation processes. Catalysts of the present invention which are suitable for use in dehydrogenation processes include platinum or palladium on steel, iron, nickel, titanium and chromium. Platinum or palladium on steel, iron or nickel are preferred.

Dehydrogenation using the catalyst of the present invention is conducted at temperatures ranging from about 60° to 300° C., preferably 100° to 250° C., and most preferably ranging from about 150° to 250°. The pressure must be sufficient to contain the linear or cycloaliphatic compound and the aromatic product. The pressure for dehydrogenation using the catalyst of the present invention ranges from autogenous pressure to 30 psi, and most preferably ranges from autogenous pressure to 20 psi.

Use of the Catalyst of the present Invention in Hydroformylation

The catalyst prepared in accordance with the process of the present invention is useful in hydroformylation, which process is well known in the art. In general, in hydroformylation an olefinic substrate, preferably an alpha-olefin, is contacted with carbon monoxide and hydrogen ($H_2$) in the presence of a homogeneous rhodium catalyst such as a rhodium carbonyl, for example, tetrarhodiumdodecacarbonyl to form an aldehyde containing one more carbon than the olefinic substrate by the addition of —H and —CHO across the carbon-carbon double bond. Rhodium on a base metal catalyst of the present invention can be used to replace colloidal rhodium catalyst used in conventional hydroformylation. The process using the catalyst of the present invention forms either a straight chain or a branched-chain aldehyde. Hydroformylation using the catalyst of the present invention is conducted at temperatures ranging from about ambient temperature to 200° C., preferably 50° C. to 150° C., and most preferably 100° C. to 150° C. The pressure of the hydroformylation reaction using the catalyst of the present invention ranges from about 100 Psi to 2000 psi, preferably about 100 psi to 1000 psi, and most preferably is about 500 psi to 800 psi.

While not wishing to be bound by theory, it is believed that the chemical cleaning agent used in the present invention removes or scours oxides, hydroxides and/or other impurities which form on the surface of the base metal upon exposure to air and moisture. Such cleaning is believed to render the surface of the base metal attractive for the adherence of a reduced noble metal specie. If a chemical cleaning agent is not used, less noble metal attaches or adheres to the base metal and a lower level of catalytic activity results. Simultaneously or sequentially to the base metal having been contacted with a chemical cleaning agent, the base metal is treated with a homogeneous noble metal-containing material (liquid or gaseous) under reducing conditions. When the base metal itself provides the reducing conditions, the oxidized noble metal specie begins to reduce. As this oxidized noble metal specie approaches the zero-valent state, it is strongly attracted to other zero-valent noble metal species and to the zero-valent base metal surface. It begins to agglomerate with other noble metal species and simultaneously deposits onto the base metal surface. Further reduction of the agglomerates so formed occurs by the continued donation of electrons from the base metal to the noble metal agglomerate, thus rendering the attachment to the base metal stronger stronger and less easily disrupted.

In the event that a chemical reducing agent other than the base metal is used, agglomeration of the noble metal specie occurs first in the solution and is followed by attachment of the agglomerate onto the base metal surface. Once again, further reduction of the agglomerates occurs by the continued donation of electrons from the base metal to the noble metal agglomerates, thus rendering attachment to the base metal surface stronger and less easily disrupted.

In the catalysts of the present invention, the noble metal specie deposited on the surface of the base metal appears to resemble the agglomerates found in a solution of a colloidal homogeneous noble metal catalyst. Hence, the heterogeneous noble metal on the base metal catalyst of the present invention behaves similarly to the homogeneous noble metal solution. However, it is further believed that, in the catalyst of the present invention, the formation of the noble metal specie does not occur strictly from the zero-valent noble metal atoms. It is believed that formation may occur from both the zero valent and from a partially oxidized specie. Thus, the agglomerate has a net positive charge and is attracted to negatively charged surfaces and ions. The base metal with its electron-rich surface can serve to displace negatively charged ions or ligands which would otherwise coat the surface of the agglomerated metal atoms, that is, the colloidal catalyst of the present invention.

Whereas the exact scope of the present invention is set forth in the appended claims, the following specific examples illustrate certain aspects of the present invention and, more particularly, point out methods of evaluating the same. However, the examples are set forth for illustration only and are not to be construed as limitations on the present invention. All parts and percentages are by weight unless otherwise specified. Reported yields are in molar percentages and are given only for the desired hydrosilation product.

In the examples which follow and throughout the specification, all temperatures are on a centigrade scale (°C.). The abbreviations/symbols cc, gm, %, ppm, Pt, ml, min, hr, mol, and m mole respectively represent cubic centimeter, gram, percent, parts per million, platinum, milliliter, minute, hour, moles, and millimole. Certain of the catalytic compositions of this invention are pyrophoric, i.e., spontaneously flammable in air, after drying.

Procedures in the examples were performed in standard laboratory glassware of various sizes or in bottles, with agitation provided by magnetic or air-driven mechanical stirrers, by rotating the glassware with a rotary evaporator, by roll milling, or by the application of ultrasound.

Examples 1 through 12 illustrate the process of preparing a catalyst of the present invention.

EXAMPLE 1

In a 500 cc, 3-necked flask equipped with an air-driven stirrer having an inert atmosphere of nitrogen were combined 300 gm of trichlorosilane, 50 gm of iron powder (325 mesh), and 10.1 cc of chloroplatinic solution (10 wt-% in 4/1 1,2-dimethoxyethane/ethanol). The mixture was stirred under ambient conditions for about three days. The iron powder was isolated by decantation of the liquid from the magnetically restrained powder, followed by washing with 100 cc aliquots of toluene and methanol until the washings with each were clear, and dried under nitrogen at 75° C. Analysis by means of atomic absorption indicated the presence of 2000 ppm of platinum. The catalyst prepared by this process was storage stable for at least several months and was used in some of the hydrosilation processes.

The procedure of Example 1 can be varied with regard to type and size of glassware, the order of reactant combination, the stirring time, and solvent washing and drying conditions. Tetrachlorosilane can be used in place of trichlorosilane.

EXAMPLE 2

An aqueous solution of chloroplatinic acid was prepared from 0.1273 gm of chloroplatinic acid hexahydrate and 50 gm of distilled water which was acidified with one drop of concentrated hydrochloric acid. Iron powder (50 gm, 300 mesh) was added and the mixture was shaken until the yellow color disappeared. The aqueous layer contained <0.1 ppm Pt. Washing with methanol and drying provided iron powder on which 728 ppm of Pt by weight had been deposited. This example demonstrates deposition of a noble metal onto a base metal from an aqueous solution.

EXAMPLE 3

In a 250 ml flask equipped as in Example 1 were combined 100 cc of methanol, 50 mmole of trimethoxysilane, and 2 mmole of chloroplatinic acid. Iron powder (20 gm, 100 mesh) was added with vigorous agitation and the mixture was heated to reflux, followed by cooling, decanting the liquid layer and washing with methanol. This example illustrates the deposition of a noble metal onto a base metal from a non-aqueous alcohol solution containing the corresponding trialkoxysilane of the alcohol.

EXAMPLE 4

Chloroplatinic acid (0.1273 gm) was dissolved in 50 gm of methanol to which one drop of concentrated hydrochloric acid had been added. Iron powder (50 gm, 100 mesh) was added and the mixture was agitated until the color of the chloroplatinic acid lightened or disappeared. The liquid was decanted, and the metal washed with fresh methanol, followed by drying under nitrogen at room temperature. This example demonstrates the deposition of a noble metal onto a base metal from a non-aqueous solution containing neither a chlorosilane nor an alkoxysilane.

EXAMPLE 5

A solution was prepared from 1.64 gm of palladium dichloride, 10 cc of distilled water, and 4 cc of concentrated hydrochloric acid. The solution was added with vigorous stirring to a mixture of 50 gm of iron powder (325 mesh) in 650 cc of distilled water. Aqueous formaldehyde (2 cc, 37%) solution was added followed by 20% aqueous sodium hydroxide until the mixture became slightly alkaline to litmus paper. The mixture was stirred for about ten minutes, filtered, and the solids washed with distilled water and methanol, followed by drying under nitrogen at 75° C. This example demonstrates the deposition of a noble metal onto a base metal from an aqueous solution using formaldehyde as the chemical reducing agent.

EXAMPLE 6

The method of Example 4 was repeated except that 0.0667 gm of palladium dichloride was substituted for the chloroplantinic acid of Example 4.

EXAMPLE 7

The method of Example 4 was repeated except that 0.1 gm of rhodium trichloride hydrate was substituted for the chloroplatinic acid of Example 4 and was dissolved in 50 gm of acidified ethanol.

EXAMPLE 8

The method of Example 4 was repeated except that 0.1 gm ruthenium trichloride hydrate was substituted for the chloroplatinic acid of Example 4 and was dissolved in 50 gm of acidified ethanol.

EXAMPLE 9

The method of Example 4 was repeated except that 0.2 gm of hexachloroiridic acid dissolved in 50 grams of acidified ethanol was substituted for the chloroplatinic acid of Example 4.

EXAMPLE 10

The procedure of Example 1 was followed except that powdered 304L stainless steel (an iron alloy) was substituted for the iron powder. Analysis by atomic absorption indicated the presence of 400 ppm of platinum.

EXAMPLE 11

Platinum was deposited on titanium powder according to the procedure of Example 1. Analysis showed 950 ppm platinum on the titanium. This material was pyrophoric, demonstrating the effectiveness of the chlorosilane cleaning agent at exposing the base metal surface.

EXAMPLE 12

Platinum was deposited on copper powder according to the procedure of Example 1. Analysis found 8500 ppm platinum on copper. This example illustrates that a platinum on copper catalyst can be prepared according to the process of the present invention. However, when the catalyst was employed in hydrosilation reactions, the catalyst proved to be inactive which is consistent with literature in reporting that copper is a poison for platinum.

Examples A through E are typical hydrosilation processes. Examples 13 through 22 illustrate that the catalyst of the present invention can be used in place of a colloidal homogeneous catalyst in hydrosilation processes. Examples 13 through 22 further illustrate the efficacy of the catalyst of the present invention in such hydrosilation processes. Example 20 illustrates a preferred embodiment for use of the catalyst of the present invention in a hydrosilation process.

EXAMPLE A

A 500 cc round-bottomed flask was fitted with an addition funnel, dry ice condenser, thermometer, gas introduction tube, and magnetic stirring bar. The flask was charged with 250 gm of o-dichlorobenzene, 0.3 ml of the chloroplatinic acid solution used in Example 1, and 0.5 gm of phenothiazine promoter. The flask was purged with acetylene and the contents heated to 100° C. Acetylene was then fed at 0.36 mol/hr through the gas introduction tube below the liquid surface, while trimethoxysilane was added from the addition funnel at 0.22 mol/hr at atmospheric pressure. After 2 hours, the trimethoxysilane feed was discontinued, and the contents of the cooled reactor were sampled. The normalized yield of vinyltrimethoxysilane was about 90%. This example demonstrates the standard reaction between acetylene and trimethoxysilane, catalyzed by chloroplatinic acid, forming vinyltrimethoxysilane.

EXAMPLE 13

The procedure of Example A was repeated except that 7.5 gm of a platinum on iron catalyst prepared according to Example 1 was used. The platinum content of this catalyst was approximately equal (within experimental reproducibility) to the platinum content of the Example A catalyst. The rate of reaction was approximately the same as in Example A, and the yield of product was 87%.

EXAMPLE 14

The method of Example 13 was followed, but using the platinum on 304L stainless steel catalyst prepared in Example 10 instead of the platinum on iron catalyst. Although the reaction appeared to be slightly slower, the product yield was similar, demonstrating that the base metal support can be an alloy.

EXAMPLE B

A 500 cc, 3-necked, round bottomed flask, equipped with a stirrer, thermometer, addition funnel, condenser and a nitrogen blow-by was charged with 138.6 grams of allyl methacrylate, which contained 50 ppm of hydroquinone inhibitor, 0.14 gm of Ionol ™ (2,6-ditertbutyl-4-methylphenol) and 0.22 ml of a 3.8% chloroplatinic acid solution in a 1,2-dimethoxyethane/ethanol mixture. The flask contents were heated to 90° C. and dropwise addition of trichlorosilane (135.5 gm, 1 mol) over a 20 minute period with cooling gave an 85% yield of 3-methacryloxypropyltrichlorosilane.

EXAMPLE 15

The procedure of Example B was repeated using 5.8 gm of a platinum on iron catalyst prepared according to Example 1. The platinum content of this catalyst was approximately equal to the platinum content of the Example B catalyst. The rate of reaction was approximately the same as in Example B, and the yield of 3-methacryloxypropyltrichlorosilane was 78%.

EXAMPLE C

The apparatus of Example B was charged with 136.8 gm (1.2 mol) of allyl glycidyl ether, 2.6 gm of a carboxylic acid promoter and 0.14 ml of 10% chloroplatinic acid solution. The addition funnel was charged with 122.8 gm (1.0 mol) of trimethoxysilane. The contents of the flask were heated to 90° C. and dropwise addition of trimethoxysilane was begun. The exotherm of the reaction was controlled with an ice bath to maintain the temperature at 90°–95° C. The addition was completed in 25 minutes and temperature was maintained at 90°–95° C. for another hour. Analysis by gas chromatography showed an 86% yield of 3-glycidoxypropyltrimethoxysilane. This example demonstrates a standard preparation of 3-9lycidoxypropyltrimethoxysilane using chloroplatinic acid solution as the catalyst.

EXAMPLE 16

The procedure of Example C was repeated except that 8.5 gm of a platinum on iron catalyst composition prepared according to Example 1 was used in place of the chloroplatinic acid. Analysis by gas chromatography showed a 77% yield of 3-glycidoxypropyltrimethoxysilane. This example shows that a platinum on iron catalyst composition of the present invention was effective as a catalyst in the hydrosilation reaction of allyl glycidyl ether and trimethoxysilane.

EXAMPLE 17

The procedure of Example 15 was repeated, but using a platinum on chromium catalyst prepared according to the method of Example 1, using chromium powder instead of iron powder. Analysis confirmed the presence of 2672 ppm platinum. The catalyst was active and a good yield of product was obtained.

EXAMPLE D

The apparatus of Example B was charged with 148.8 g (1.2 mol) of 1-vinyl-3,4-epoxycyclohexane, 1.3 g of a carboxylic acid promoter, and 0.15 ml 0f 10% chloroplatinic acid catalyst solution. The flask contents were heated to 89° C. and dropwise addition of 122.8 g (1.0 mol) of trimethoxysilane was begun. The reaction temperature was controlled at 90°-95° C. with an ice bath. Reaction was maintained at that temperature for half an hour after completion of addition, which took 18 minutes. Analysis by gas chromatography showed a yield of 90% of 2-(3,4-epoxycyclohexyl)ethyltrimethoxysilane. This example demonstrates a standard preparation of 2-(3,4-epoxycyclohexyl)ethyltrimethoxysilane using commercial chloroplatinic acid.

EXAMPLE 18

The reaction of Example D was repeated except that 11.5 gm of platinum on iron prepared according to Example 1 was used as the catalyst in place of the chloroplatinic acid solution. A very low yield of product (2-3%) was obtained. It is believed that the chloroplatinic acid catalyst in Example D remains as a true homogeneous catalyst and is not reduced to a colloidal form. It is further believed that the catalyst of the present invention does not work well in reactions or processes such as those of Example D which reactions require a truly homogeneous (non-colloidal) catalyst.

EXAMPLE E

To a tubular reactor was fed a mixture of acetylene and trichlorosilane containing 0.01% of a solution of 10% chloroplatinic acid in a mixture of 1,2-dimethoxyethane and ethanol. Upon heating to 85° C., the reaction mixture exothermed to 270° C. and sustained this temperature while feed continued. A yield of 85% of vinyltrichlorosilane was formed. It has been observed by those skilled in the art that if no platinum, as chloroplatinic acid, is fed, no exotherm occurs, and no yield of product is obtained. This example illustrates the use of the standard chloroplatinic acid as catalyst for hydrosilation of acetylene with trichlorosilane.

EXAMPLE 19

The reactor of Example E was equipped with a carbon steel spirally wound wire as a heat transfer enhancement element such as that which is available from Cal-Gavin (Birmingham, England). The wire had been previously treated with a solution of chloroplatinic acid in tetrachlorosilane. Identical flow rates of reactants (trichlorosilane and acetylene) but with no added catalyst were used in the reactor. Considerably enhanced catalytic activity was observed in this reactor since it was observed that the exotherm initiated at 60° C. when compared to the identical reactor with an untreated heat transfer enhancement element (Example E) which exothermed at 85° C. This example demonstrates that platinum deposited on a base metal is a catalyst in the reaction of acetylene with trichlorosilane to produce vinyltrichlorosilane in a continuous plug-flow or tubular reactor.

EXAMPLE 20

A glass reactor capable of sustaining moderate pressure (20 psig) fitted with a mechanical stirrer is plumbed to receive acetylene gas fed by pressure and trimethoxysilane fed by a liquid feed pump. The reactor is filled two-thirds full with vinyltrimethoxysilane and 50 gms of the platinum on iron powder catalyst of Example 3. The reactor is also filled with a discharge tube, which extends below the surface of the liquid, leading to a pump. The discharge pump rate is set to equal the pump rate at which trimethoxysilane is introduced to the reactor. The trimethoxysilane feed contains 1 ppm dissolved platinum (as chloroplatinic acid). The reactor is heated to 100° C. and the feed and discharge pumps started. Acetylene gas is fed to the reactor on demand to maintain constant pressure. Hydrosilation of acetylene with trimethoxysilane proceeds smoothly over a period of days, with product being withdrawn as rapidly as it is formed. The platinum on iron powder catalyst remains in the reactor by virtue of gravitational settling inside the discharge tube, and the catalytic surface of the platinum on iron is refreshed by the presence of chloroplatinic acid in solution, thus maintaining a constant level of catalytic activity. It is anticipated that the amount of platinum fed to the reactor is thereby reduced more than ten fold over that disclosed in U.S. Pat. No. 5,041,595.

EXAMPLE 21

Reuse of Catalyst

At the conclusion of an experimental run as in Example 13 the platinum on iron catalyst was evaluated for reuse or recycling. At the end of the reaction, a magnet was used to hold the platinum on iron powder catalyst in the flask while the liquid product was decanted. The liquid product was clear and had a platinum content of less than 0.1 ppm. A yield of 80% product was obtained. The catalyst was left in the flask, and more reagents added. The reaction proceeded smoothly, and gave a 55% yield of product. This example illustrates the ease of separation of the noble metal catalyst, that the catalyst is heterogeneous in physical form, and that the catalyst can be reused or recycled.

EXAMPLE 22

The tenacity or ability of the noble metal to adhere to the base metal support of the catalyst of the present invention was examined. A platinum on iron catalyst was prepared as in Example 1. Aliquots of the iron powder were taken at various intervals during the reaction (hydrosilation). These aliquots were analyzed for platinum and chlorine content. The results are summarized in Table 1.

TABLE 1

| | Pt Conc., ppm | Cl Conc., % |
|---|---|---|
| As prepared, before washing | 8000 | 2.1 |
| One toluene wash | 7300 | 1.9 |
| One toluene/methanol wash | 2000 | 0.01 |

Further washing did not reduce the platinum content, within experimental error.

Examples F and G are a typical deamination process and illustrate the effectiveness of two different commercial palladium catalysts in the deamination of 3-glycidoxypropyltrimethoxysilane. Examples 23 through 26 illustrate the use of the catalyst of the present invention in such a deamination process.

EXAMPLE F

The apparatus of Example A was charged with 180 gm of 3-aminopropyltrimethoxysilane and 0.15 gm of commercially available palladium dichloride (500 ppm of palladium). The flask contents were heated to 180° C. while hydrogen was bubbled through the liquid at 50 ml/min. Ammonia evolved continuously, and analysis by gas chromatography of the flask contents after 7 hours showed that 25% of the original silane had been converted to bis-(3-trimethoxysilylpropyl)amine and other higher boiling products.

EXAMPLE G

Example F was repeated using a commercial 5% palladium on carbon catalyst which converted 71% of the original silane after 15 hr at 180° C. (1000 ppm of palladium).

Examples 23 and 24 demonstrate that a noble metal (palladium) deposited on a base metal (iron) is effective in deaminating 3-glycidyloxypropyltrimethoxysilane.

EXAMPLE 23

The reaction of Example F was repeated except that a palladium on iron catalyst composition prepared according to the method of Example 2 was used. A 29% conversion of the original silane resulted after 9 hours at 180° C.

EXAMPLE 24

The reaction of Example G was repeated except that a palladium on iron catalyst prepared as in Example 6 was used. An 8% conversion of the original silane after 6.5 hours at 180° C. was observed.

EXAMPLE 25

The deamination procedure of Example 23 was followed, except that a palladium on nickel catalyst, prepared according to the procedure of Example 6, that is, palladium on a different base metal, was used. Evolution of ammonia was rapid, and conversion to the bis-(trimethoxysilylpropyl)amine product occurred as confirmed by gas chromatography analysis.

EXAMPLE 26

Amination

In accordance with the procedure set forth in U.S. Pat. No. 4,526,996, in an autoclave capable of containing pressure to 1000 psi are placed 2-cyanoethyltrimethoxysilane, a stoichiometric excess of piperazine, and a rhodium on base metal catalyst prepared as in Example 7. The autoclave is sealed, purged with hydrogen, and pressurized with hydrogen. After prolonged heating to about 135° C., the autoclave is cooled and opened and is found to contain N-(3-triethoxysilylpropyl)piperazine.

EXAMPLE 27

Gas Phase Preparation of Catalyst and Hydrogenation

A tubular reactor fitted with a spirally-wound wire heat transfer element is heated to 500° C. under an atmosphere of flowing carbon monoxide for several hours. After cooling under a stream of nitrogen heated to 100° C., a volatile rhodium noble metal complex is introduced to the gaseous stream by causing the heated nitrogen to flow across the solid noble metal complex. Rhodium noble metal aggregates are deposited on the surfaces of the reactor, particularly including the spirally wound steel wire heat transfer element. Subsequent introduction of ethylene and hydrogen into the reactor at 100° C. results in hydrogenation of the ethylene.

EXAMPLE 28

Dehydrogenation

The reactor of Example 27, containing a platinum on steel wire catalyst (the spirally wound heat transfer element) is heated to 200° C. under a stream of nitrogen. Cyclohexene vapor is introduced into the stream, along with a trace of hydrogen. The product stream exiting the reactor contains benzene and cyclohexane in an approximately 1:2 weight ratio, along with unreacted cyclohexene.

EXAMPLE 29

Hydroformylation

In an autoclave capable of containing 1000 psig is placed an alpha-olefinic substrate such as propylene, a hydrocarbon solvent such as toluene, and a rhodium on iron metal catalyst prepared according to the process of the present invention. The contents of the autoclave are heated to about 150° C. The autoclave is pressurized with equal volumes of hydrogen and carbon monoxide gases and brought to a total pressure of about 800 psi. When uptake of the gases ceases, the gas feed is stopped, and the reactor is cooled. After cooling, the autoclave is opened and the product such as butyraldehyde is removed.

EXAMPLES H-J and 30-34

Dehydrocondensation Processes

A 1/1 mixture by weight of methanol/trimethoxysilane was prepared. Ten milliliter aliquots of this mixture were added to 25-ml test tubes containing the catalyst materials set forth in Table 2. Visual observation was used to estimate catalytic activity based on rates of hydrogen evolution on an arbitrary scale of 0 to 10 with a designation of 10 being the most active. The results of these experiments are summarized in Table 2 and compare the catalytic activity for noble metals deposited on base metals to iron powder and to some commercially available materials.

Table 2 shows that the activity of the noble metal (platinum) can be modified and/or controlled by depositing it on different base metals. Examples 30 through 34 illustrate the efficacy of the catalysts of the present invention in dehydrocondensation processes.

TABLE 2

CATALYST ACTIVITY
MeOH/HSi(OMe)₃
DEHYDROCONDENSATION REACTION

| Example | Catalytic Material | Activity[1] | Amount |
|---|---|---|---|
| H | Fe Powder | 1-2 | 0.1 gm |
| I | Pt on Carbon | 5-6 | 0.3 gm of 5% Pt/C |
| J | CPA[2] | 9 | 0.1 ml of 10% CPA solution |
| 30 | Pt on Iron | 5-8 | 0.1 gm of 2000 ppm Pt |
| 31 | Pt on Cr | 1-2 | 0.1 gm of 8672 ppm Pt |
| 32 | Pt on Cu | 2 | 0.1 gm of 8444 Pt |
| 33 | Pt on Ni | 0 | 0.1 gm of 3618 ppm Pt |
| 34 | Pt on Ti | 2-3 | 0.1 gm of 956 ppm Pt |

[1] 0 = No Activity 10 = High Activity
[2] CPA = chloroplatinic acid

Examples K through O and 35 through 43 illustrate the susceptibility of various platinum catalysts to mercury poisoning. In general, colloidal catalysts are susceptible to mercury poisoning, while non-colloidal catalysts are not. The results of the effect of mercury poisoning are set forth in Tables 3 and 4.

EXAMPLE K

The procedure of Example C was followed, except that one drop of metallic mercury was added immediately after beginning the addition of trimethoxysilane. No reaction was observed, and only a trace of 3-glycidoxypropyltrimethoxysilane was produced. The mercury poisoned the colloidal homogeneous platinum catalyst, as reported in the literature.

EXAMPLE L

The procedure of Example C was followed, using 5 gm of 5% platinum on alumina commercial catalyst, instead of chloroplatinic acid. No mercury was added. The reaction proceeded smoothly, giving a 75% yield of 3-glycidoxypropyltrimethoxysilane.

EXAMPLE M

Example L was repeated, but one drop of metallic mercury was added immediately after addition of trimethoxysilane was begun. A 73% yield of 3-glycidoxypropyltrimethoxysilane was obtained. Thus, mercury did not poison the heterogeneous platinum catalyst, consistent with reports in the literature on similar catalysts.

EXAMPLE N

Example C was repeated, except that tetrakis(triphenylphosphine) platinum was used as the catalyst instead of chloroplatinic acid. No mercury was added. A 75% yield of 3-glycidoxypropyltrimethoxysilane was obtained.

EXAMPLE O

Example N was repeated, except that one drop of metallic mercury was added immediately after addition of trimethoxysilane was begun. Reaction proceeded smoothly, giving a 79% yield of 3-glycidoxypropyltrimethoxysilane. This demonstrates that mercury does not poison a truly homogeneous noble metal catalyst, as reported in the literature.

EXAMPLES 35-43

The procedure of Example 13 was followed, except that one drop of metallic mercury was added, either before, immediately following, or after addition of trimethoxysilane was begun. In every case, catalytic activity was either eliminated or severely reduced. The results, summarized in Table 3, demonstrate that the platinum on iron catalyst is poisoned by mercury, but not as completely as a typically colloidal platinum catalyst such as that used in Example K.

TABLE 3

| Example | When Mercury Added | Result |
|---|---|---|
| 35 | before TMS* | reaction started, poor yield |
| 36 | before TMS* | reaction started, then died |
| 37 | before TMS* | reaction never started |
| 38 | immediately after TMS addition begun | reaction started, died |
| 39 | immediately after TMS addition begun | reaction started, died |
| 40 | immediately after TMS addition begun | reaction started, died |
| 41 | after TMS addition begun, exotherm observed | 18% yield |
| 42 | after TMS addition begun, exotherm observed | 57% yield |
| 43 | after TMS addition begun, exotherm observed | 12% yield |

*TMS = trimethoxysilane

TABLE 4

Examples Differentiating Types of Catalyst by the Mercury Poisoning Effect

| Example | Catalyst | Mercury Added | Result | Conclusion |
|---|---|---|---|---|
| C | chloroplatinic acid | No | 86% yield | |
| J | chloroplatinic acid | Yes | Poisoned; 0% yield | Pt is colloidal |
| K | Pt on alumina | No | 75% yield | |
| L | Pt on alumina | Yes | not poisoned; 73% yield | Pt is not colloidal; it is crystallite |
| M | Pt(triphenylphosphine)₄ | No | 75% yield | |
| N | Pt(triphenylphosphine)₄ | Yes | not poisoned; 79% yield | Pt is monatomic (truly homogeneous) |
| 13 | Pt on iron | No | 77% yield | |
| 35-43 | Pt on iron | Yes (poisoned at varying times) | poisoned; yields varied from 0-57%, depending on when mercury was added. | Pt is colloidal |

What is claimed is:

1. An electroless process for making a catalyst having a noble metal deposited on a base metal, which process comprises in a liquid or gaseous medium
    (1) contacting a base metal with a chemical cleaning agent selected from the group consisting of a chlorosilane, an alkoxysilane and a non-oxidizing acid, and
    (2) treating said base metal under reducing conditions with a noble metal-containing material.

2. The process of claim 1 wherein the contacting and treating steps are carried out sequentially.

3. The process of claim 1 wherein the contacting and treating steps are carried out simultaneously.

4. The process of claim 1 wherein the base metal is selected from the group consisting of titanium, vanadium, chromium, manganese, molybdenum, tungsten, iron, cobalt, nickel, copper, zinc, and alloys thereof.

5. The process of claim 4 wherein the base metal is selected from the group consisting of iron, nickel, chromium, and alloys thereof.

6. The process of claim 4 wherein the noble metal-containing material contains at least one noble metal selected from the group consisting of platinum, iridium, ruthenium, rhodium and palladium.

7. The process of claim 4 wherein said noble metal-containing material is a homogeneous noble metal solution.

8. The process of claim 7 wherein the homogeneous noble metal solution contains (i) at least one noble metal halide, noble metal-containing complex or a salt of a noble metal halide and (ii) a solvent therefor.

9. The process of claim 7 wherein the homogeneous noble metal solution comprises:
   (i) a platinum halide, a salt of a platinum halide or a mixture thereof, and
   (ii) a solvent selected from the group consisting of water, cyclic and linear ethers, alcohols and mixtures thereof, and wherein the base metal is selected from the group consisting of iron, nickel, and alloys thereof.

10. The process of claim 9 wherein the platinum halide or salt thereof is selected from the group consisting of $H_2PtCl_6$, $Na_2PtCl_6$, $Na_2PtCl_4$ and mixtures thereof, and the solvent is selected from the group consisting of tetrahydrofuran, 2-propanol, ethanol, 1,2-dimethoxyethane and mixtures thereof.

11. The process of claim 7 wherein the homogeneous noble metal solution comprises (i) at least one platinum complex and (ii) a solvent selected from the group consisting of aromatic hydrocarbons, chlorinated aliphatic and aromatic hydrocarbons and mixtures thereof; and wherein the base metal is selected from the group consisting of iron, nickel, and alloys thereof.

12. The process of claim 11 wherein the platinum complex is selected from the group consisting of $Pt(2,4$-pentanedioate$)_2$, $PtCl_2$(triphenylphosphine$)_2$ and mixtures thereof, and the solvent is selected from the group consisting of methylene chloride, toluene, o-dichlorobenzene and mixtures thereof.

13. The process of claim 7 wherein the homogeneous noble metal solution comprises (i) a palladium halide, a salt of a palladium halide or a mixture thereof; and (ii) a solvent selected from the group consisting of water and an aliphatic alcohol having 1 to 3 carbon atoms, and mixtures thereof; and wherein the base metal is selected from the group consisting of titanium, iron, nickel, copper, and alloys thereof.

14. The process of claim 13 wherein the palladium halide or salt thereof is selected from the group consisting of $PdCl_2$, $Na_2PdCl_4$, $Na_2PdCl_2$ and mixtures thereof, and the solvent is selected from the group consisting of water, methanol, and mixtures thereof.

15. The process of claim 7 wherein the homogeneous noble metal solution comprises (i) at lease one palladium complex and (ii) a solvent selected from the group consisting of chlorinated hydrocarbons having 1 to 6 carbon atoms, linear and cyclic ethers having 4 to 6 carbon atoms and mixtures thereof.

16. The process of claim 7 wherein the homogeneous noble metal solution comprises (i) a ruthenium halide or salt thereof and (ii) a solvent selected from the group consisting of water, a linear and branched aliphatic alcohol having 1 to 3 carbon atoms, linear and cyclic ethers having 4 to 6 carbon atoms and mixtures thereof; and wherein the base metal is selected from the group consisting of iron, cobalt, nickel, copper, and alloys thereof.

17. The process of claim 7 wherein the homogeneous noble metal solution comprises (i) at least one ruthenium complex and wherein the base metal is selected from the group consisting of iron, cobalt, nickel, copper, and alloys thereof.

18. The process of claim 7 wherein the homogeneous noble metal solution comprises (i) a rhodium halide or salt thereof and (ii) a solvent selected from the group consisting of water, linear and branched aliphatic alcohols having 1 to 3 carbon atoms, linear and cyclic ethers having 4 to 6 carbon atoms, and wherein the base metals are selected from the group consisting of titanium, manganese, iron, cobalt, nickel, and alloys thereof.

19. The process of claim 7 wherein the homogeneous noble metal solution comprises (i) at least one rhodium complex and wherein the base metal is selected from the group consisting of titanium, manganese, iron, cobalt, nickel, and alloys thereof.

20. The process of claim 7 wherein the homogeneous noble metal solution comprises (i) an iridium halide or salt thereof and (ii) a solvent selected from the group consisting of water, linear and branched aliphatic alcohols having 1 to 3 carbon atoms, linear and cyclic ethers and mixtures thereof and wherein the base metal is selected from the group consisting of titanium, iron, nickel, and alloys thereof.

21. The process of claim 7 wherein the homogeneous noble metal solution comprises (i) at least one iridium complex and wherein the base metal is selected from the group consisting of titanium, iron, nickel, and alloys thereof.

22. The process of claim 8 wherein the amount of the noble metal halide or salt thereof, or of the noble metal complex ranges from about 0.02 to 2.0 weight percent, based upon the amount of base metal.

23. The process of claim 1 wherein reducing conditions are provided by a chemical reducing agent selected from the group consisting of:
   (i) a silane having the formula:

$(R)_y Si(H)_x$ wherein x and y are each individually at least 1, $x + y = 4$, and R is the same or different and is selected from the group consisting of a halogen, an alkoxy group having 1 to 5 carbon atoms, an alkyl group having 1 to 6 carbon atoms, and a haloalkyl group having 1 to 4 carbon atoms,
   (ii) formaldehyde, and
   (iii) a base metal having a reduction potential higher than that of the noble metal.

24. The catalyst produced by the process of claim 1.

* * * * *